(12) United States Patent
Njardarson et al.

(10) Patent No.: US 10,358,438 B2
(45) Date of Patent: Jul. 23, 2019

(54) [3+2] ANNULATION TO PRODUCE 5-MEMBERED HETEROCYCLIC COMPOUNDS

(71) Applicant: THE ARIZONA BOARD OF REGENTS ON BEHALF OF THE UNIVERSITY OF ARIZONA, Tucson, AZ (US)

(72) Inventors: Jon T. Njardarson, Tucson, AZ (US); Isaac Chogii, Tucson, AZ (US); David Townsend Smith, Tucson, AZ (US); Edon Vitaku, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 117 days.

(21) Appl. No.: 15/329,615

(22) PCT Filed: Jul. 20, 2015

(86) PCT No.: PCT/US2015/041169
§ 371 (c)(1),
(2) Date: Jan. 27, 2017

(87) PCT Pub. No.: WO2016/014426
PCT Pub. Date: Jan. 28, 2016

(65) Prior Publication Data
US 2017/0253580 A1 Sep. 7, 2017

Related U.S. Application Data

(60) Provisional application No. 62/027,209, filed on Jul. 21, 2014, provisional application No. 62/038,143, filed on Aug. 15, 2014, provisional application No. 62/131,948, filed on Mar. 12, 2015.

(51) Int. Cl.
| | | |
|---|---|---|
| *C07D 405/04* | (2006.01) | |
| *C07D 209/42* | (2006.01) | |
| *C07D 207/48* | (2006.01) | |
| *C07D 207/18* | (2006.01) | |
| *C07D 207/277* | (2006.01) | |
| *C07D 209/12* | (2006.01) | |

(52) U.S. Cl.
CPC ......... *C07D 405/04* (2013.01); *C07D 207/18* (2013.01); *C07D 207/277* (2013.01); *C07D 207/48* (2013.01); *C07D 209/12* (2013.01); *C07D 209/42* (2013.01)

(58) Field of Classification Search
None
See application file for complete search history.

(56) References Cited

PUBLICATIONS

Aldous et al., The dihydrofuran template approach to furofuran synthesis. Organic & Biomolecular Chemistry, 2006, 4, 2912-2927.*

* cited by examiner

Primary Examiner — Po-Chih Chen
(74) Attorney, Agent, or Firm — Don D. Cha; HDC IP Law, LLP

(57) ABSTRACT

The present invention relates to various organic reactions including a method for producing heterocyclic compounds using a [3+2] annulation; a method for producing fluorinated heteroaromatic compounds; and a method for alkylating a meta-position of a phenolic compound.

12 Claims, 2 Drawing Sheets

[3+2] ANNULATION TO PRODUCE 5-MEMBERED HETEROCYCLIC COMPOUNDS

CROSS-REFERENCE TO RELATED APPLICATIONS

This application claims the priority benefit of U.S. Provisional Application Nos. 62/027,209, filed Jul. 21, 2014; 62/038,143, filed Aug. 15, 2014; and 62/131,948, filed Mar. 12, 2015, all of which are incorporated herein by reference in their entirety.

FIELD OF THE INVENTION

The present invention relates to various organic reactions including a method for producing heterocyclic compounds using a [3+2] annulation; a method for producing fluorinated heteroaromatic compounds; and a method for alkylating a meta-position of a phenolic compound.

BACKGROUND OF THE INVENTION

While a variety of chemical reactions are available for transforming one compound to another, each of reaction has its own limitation(s). For example, some reactions only yield a particular substitution pattern. Others produce a low yield and/or undesired side-products. Still others require expensive reagents and/or harsh reaction conditions.

Accordingly, there is a continuing need for new organic reactions to overcome various limitations of conventional methods.

SUMMARY OF THE INVENTION

The present invention provides various organic reactions. In one aspect of the invention, a method is provided for producing a 3-pyrroline compound of the formula:

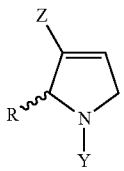

I

In this aspect of the invention, the method includes deprotonating an α,β-unsaturated compound of the formula:

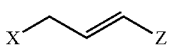

II with a base under condition sufficient to produce a deprotonated intermediate; and reacting said deprotonated intermediate an imine compound of the formula:

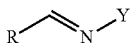

III under conditions sufficient to produce said 3-pyrroline compound, where R is hydrogen, alkyl, haloalkyl, aryl, aralkyl, alkenyl, aralkenyl, cycloalkyl, heteroalkyl, heteroaryl or ester functional group; X is a leaving group; Y is an auxiliary group; and Z is an electron withdrawing conjugated group.

In one particular embodiment, Y is a chiral auxiliary group. In some instances, the chiral auxiliary group is a moiety of the formula:

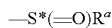

IV where * denotes a chiral center; and $R^a$ is alkyl, cycloalkyl, aralkyl, alkenyl, aralkenyl, heteroalkyl, or heteroaryl.

In another embodiment, the imine compound of Formula III has enantiomeric excess of at least 99% e.e. In this manner, the 3-pyrroline compound that is produced is diastereomerically enriched. It should be appreciated that diastereromeric and/or enantiomeric enrichment of a product refers to diastereomeric and/or enantiomeric enrichment, respectively, prior to any separation of the isomers. In some instances, the diastereomeric excess of said 3-pyrroline compound is at least 95% d.e.

Another aspect of the invention provides a process for producing a fluoroalkyl-substituted heteroaryl compound of the formula:

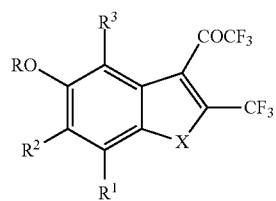

IA

In this aspect of the invention, the method includes contacting an aromatic compound of the formula:

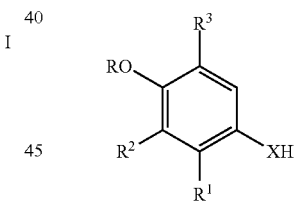

IIA with hexafluoroacetylacetone (Hfacac) under conditions sufficient to produce an intermediate; and contacting said intermediate with an acid under conditions sufficient to produce a fluoroalkyl-substituted compound of Formula IA, where R is alkyl; X is —$NR^a$—, wherein $R^a$ is hydrogen, alkyl or a nitrogen protecting group; and each of $R^1$, $R^2$ and $R^3$ is independently hydrogen, alkyl, haloalkyl, halide, vinyl, alkynyl, CHO, C(=O)$R^b$ (ketone), $CO_2R^c$ (ester), $OR^d$, $OSO_2R^e$, aryl and heteroaryl, wherein each of $R^b$, $R^c$, $R^d$, and $R^e$ is independently alkyl or aryl.

In some embodiments, said step of producing said intermediate further comprises adding phenyliodine diacetate, PhI=O, PhI(OCOR$^f$)$_2$, ArylI(OCOR$^f$)$_2$, Pb(OCOR$^f$)$_4$, or a combination thereof, wherein each of $R^f$ is independently alkyl or aryl. In some instances, said step of producing said intermediate further comprises adding phenyliodine diacetate. Typically, at least 1 equivalence of phenyliodine diacetate, relative to the amount of said aromatic compound of Formula IIA, is added to the reaction mixture.

In another embodiment, the amount of Hfacac used is at least 1 equivalence relative to the amount of said aromatic compound of Formula IIA.

Yet in other embodiments, said acid comprises organic acid, hydrochloric acid, sulfuric acid, phosphoric acid, a Lewis acid, or a combination thereof.

Still another aspect of the invention provides a process for producing a fluoroalkyl-substituted heteroaryl compound of the formula:

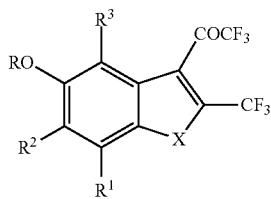

IA

In this aspect of the invention, the process comprises (i) adding hexafluoroacetylacetone (Hfacac) to a solution of phenyliodine diacetate to produce a reactive intermediate solution; (ii) adding an aromatic compound of the formula:

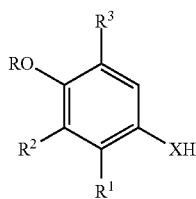

IIA to said reactive intermediate solution under conditions sufficient to produce an intermediate; and (iii) contacting said intermediate with an acid under conditions sufficient to produce a fluoroalkyl-substituted compound of Formula IA, where R is alkyl; X is —$NR^a$—, wherein $R^a$ is hydrogen, alkyl or a nitrogen protecting group; and each of $R^1$, $R^2$ and $R^3$ is independently hydrogen, alkyl, haloalkyl, halide, vinyl, alkynyl, CHO, C(=O)$R^b$ (ketone), $CO_2R^c$ (ester), $OR^d$, $OSO_2R^e$, aryl and heteroaryl, wherein each of $R^b$, $R^c$, $R^d$, and $R^e$ is independently alkyl or aryl.

Generally, said acid comprises organic acid, hydrochloric acid, sulfuric acid, phosphoric acid, a Lewis acid, or a combination thereof.

Yet another aspect of the invention provides a compound of the formula:

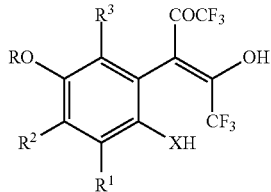

where R is alkyl; X is —$NR^a$—, wherein $R^a$ is hydrogen, alkyl or a nitrogen protecting group; and each of $R^1$, $R^2$ and $R^3$ is independently hydrogen, alkyl, haloalkyl, halide, vinyl, alkynyl, CHO, C(=O)$R^b$ (ketone), $CO_2R^c$ (ester), $OR^d$, $OSO_2R^e$, aryl and heteroaryl, wherein each of $R^b$, $R^c$, $R^d$, and $R^e$ is independently alkyl or aryl.

Another aspect of the invention provides a method for alkylating a phenolic compound with an alkylating agent, said method comprising: (a) contacting a phenolic compound with an oxidizing agent under conditions sufficient to produce a reactive intermediate compound; and (b) contacting said reactive intermediate compound with an alkylating agent under conditions sufficient to produce a meta-alkyl substituted phenolic compound.

In one embodiment, said oxidizing agent comprises ArI(OC(=O)R)$_2$, Pb(OC(=O)R)$_4$, or a combination thereof, wherein each of R is independently an alkyl, haloalkyl, cycloalkyl, optionally substituted aryl, aralkyl or (cycloalkyl)alkyl; and Ar is an aryl group, which can be optionally substituted with carbon atoms or other heteroatoms, including but not limited to halogens (F, Cl), nitrogen, oxygen, or sulfur containing functionalities.

Still in another embodiment, said alkylating agent is a compound of the formula $R^1B((X)_nR^2)((X)_nR^3)$, wherein $R^1$ is alkyl, each n is independently 0 or 1, each of $R^2$ and $R^3$ is independently alkyl, or $R^2$ and $R^3$ together with the atom to which they are attached to form a cyclic moiety.

Yet in another embodiment, the method further comprises the steps of contacting said meta-alkyl substituted phenolic compound with an electrophilic moiety to produce a meta-alkyl substituted phenolic compound comprising an electrophilic substituent. In some instances, said electrophilic moiety is present as a substituent within said phenolic compound.

Typically, the reaction temperature of said step (a) is about 50° C. or less. Often the reaction temperature of said step (a) is about 25° C. or less.

Still yet in another embodiment, said phenolic compound further comprises an ortho-substituted electron donating group.

BRIEF DESCRIPTION OF THE INVENTION

DETAILED DESCRIPTION OF THE INVENTION

Figure 1:
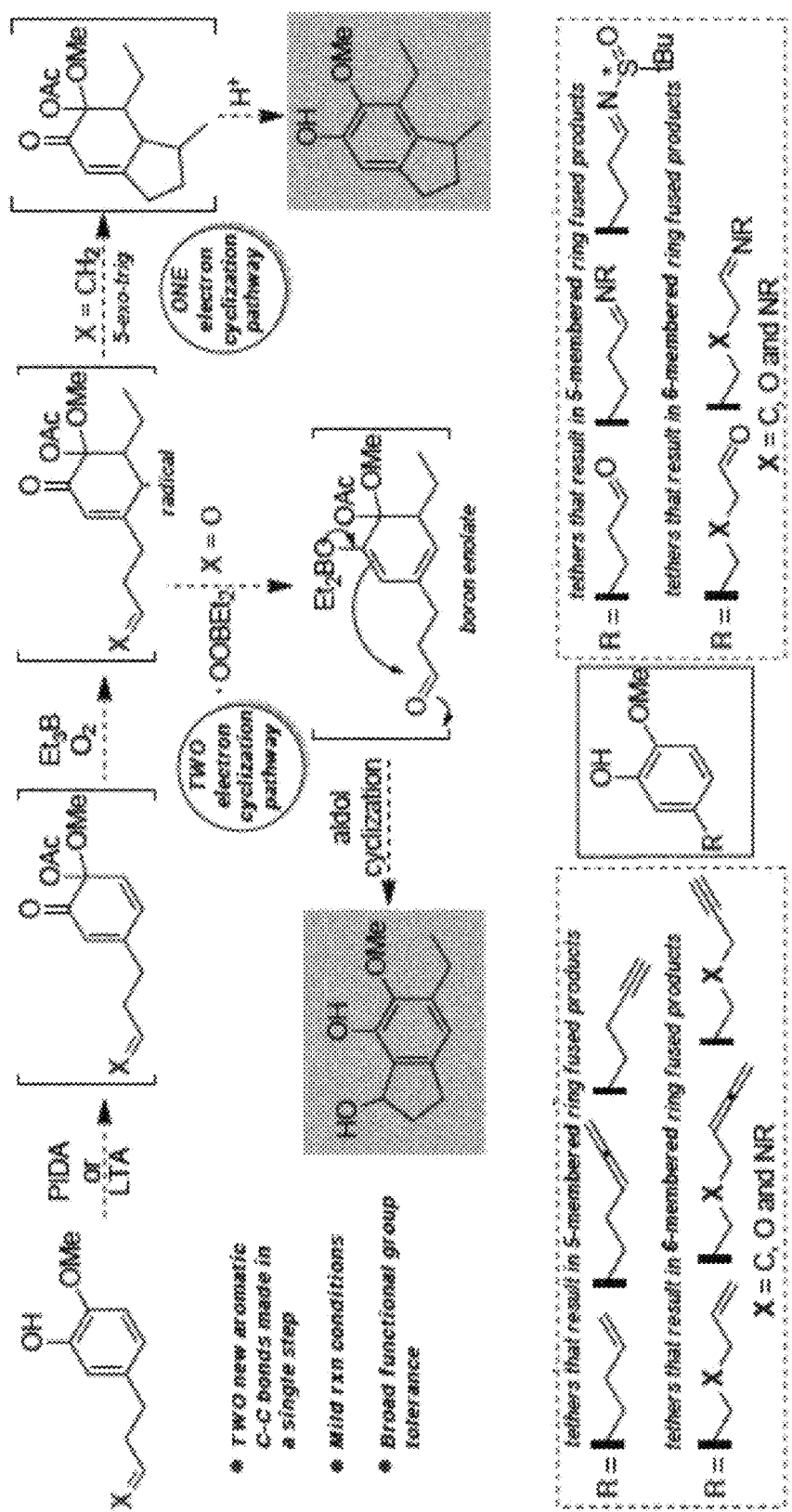
FIG. 1 is a schematic illustration of reaction scheme for electrophilic reaction of alkylated phenolic compounds.

"Alkyl" refers to a saturated linear monovalent hydrocarbon moiety of one to twelve, typically one to six, carbon atoms or a saturated branched monovalent hydrocarbon moiety of three to twelve, preferably three to six, carbon atoms. Exemplary alkyl group include, but are not limited to, methyl, ethyl, n-propyl, 2-propyl, tent-butyl, pentyl, and the like.

The term "alkoxy" refers to a moiety of the formula —$OR^1$, where $R^1$ is alkyl as defined herein.

"Alkylene" refers to a saturated linear divalent hydrocarbon moiety of one to twelve, typically one to six, carbon atoms or a branched saturated divalent hydrocarbon moiety of three to twelve, preferably three to six, carbon atoms. Exemplary alkylene groups include, but are not limited to, methylene, ethylene, propylene, butylene, pentylene, and the like.

"Alkylene" refers to a saturated linear divalent hydrocarbon moiety of one to twelve, typically one to six, carbon atoms or a branched saturated divalent hydrocarbon moiety of three to twelve, typically three to six, carbon atoms. Exemplary alkylene groups include, but are not limited to, methylene, ethylene, propylene, butylene, pentylene, and the like.

"Alkenyl" refers to a linear monovalent hydrocarbon moiety of two to twelve, typically two to six carbon atoms or a branched monovalent hydrocarbon moiety of three to twelve, typically, three to six carbon atoms, containing at least one double bond. Exemplary alkenyl groups include ethenyl (i.e., vinyl), propenyl, and the like.

"Alkynyl" refers to a linear monovalent hydrocarbon moiety of two to twelve, typically two to six carbon atoms or a branched monovalent hydrocarbon moiety of three to twelve, typically, three to six carbon atoms, containing at least one carbon-carbon triple bond. Exemplary alkenyl groups include ethynyl, propynyl, and the like.

"Aryl" refers to a monovalent mono-, bi- or tricyclic aromatic hydrocarbon moiety of 6 to 15 ring atoms which is optionally substituted with one or more, preferably one, two, or three substituents within the ring structure. When two or more substituents are present in an aryl group, each substituent is independently selected. Exemplary substituents for the aryl group include, but are not limited to, alkyl, haloalkyl, thioalkyl, heteroalkyl, halo, nitro, cyano, cycloalkyl, aryl, heteroaryl, heterocyclyl, haloalkoxy, aryloxy, heteroaryloxy, etc.

"Aralkyl" refers to a moiety of the formula —$R^bR^c$ where $R^b$ is an alkylene group and $R^c$ is an aryl group as defined herein. Exemplary aralkyl groups include, but are not limited to, benzyl, phenylethyl, 3-(3-chlorophenyl)-2-methylpentyl, and the like.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image.

"Cycloalkyl" refers to a non-aromatic, preferably saturated, monovalent mono- or bicyclic hydrocarbon moiety of three to ten ring carbons. The cycloalkyl can be optionally substituted with one or more, preferably one, two, or three, substituents within the ring structure. When two or more substituents are present in a cycloalkyl group, each substituent is independently selected. Exemplary substituents for cycloalkyl group include, but are not limited to, alkyl, haloalkyl, halo, nitro, cyano, heteroalkyl, aryl, heteroaralkyl, etc.

"Cycloalkylalkyl" refers to a moiety of the formula —$R^dR^e$ where $R^d$ is an alkylene group and $R^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

"Heterocyclyl" means a non-aromatic monocyclic moiety of three to eight ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocyclyl ring can be optionally substituted independently with one or more, preferably one, two, or three, substituents. When two or more substituents are present in a heterocyclyl group, each substituent is independently selected. Exemplary substituents for heterocyclyl group include, but are not limited to, alkyl, haloalkyl, heteroalkyl, halo, nitro, cyano, aryl, heteroaryl, aralkyl, heteroaralkyl, etc.

"Enantiomeric excess" refers to the difference between the amount of enantiomers. The percentage of enantiomeric excess (% e.e, or % ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%-1% or 98%.

"Diastereomeric excess" refers to the difference between the amount of diastereomers. The percentage of diastereomeric excess (% d.e, or % de) can be calculated by subtracting the percentage of one diastereomer from the percentage of the other diastereomers. For example, if the % de of (R,R)-diastereomer is 99% and % de of all other diastereomers (e.g., (R,S)-, (S,S)- and (S,R)-diastereomers) is 1%, the % de of (R,R)-isomer is 99%-1% or 98%.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like. Specific examples of leaving groups include, but are not limited to, Cl, Br, I and sulfonate esters such as OMs (mesylate), OTs (tosylate), ONs (nosylate), OTf (triflate) and any other sulfonate esters.

The term "electron withdrawing group" refers an atom or a functional group that removes electron density from a conjugated π system via resonance or inductive electron withdrawal, thus making the π system more electrophilic. Exemplary electron withdrawing groups that are useful in the invention include, but are not limited to, esters, sulfones, aldehydes, nitro groups (—$NO_n$, where n is 1 or 2), nitriles, halides, amides, ketones, heteroaryls, as well as other heteroatom containing functional groups.

The term "α,β-unsaturated compound" refers to any compound that has α,β-unsaturation near the electron withdrawing group. Such a compound can be generally represented as $R^a$—$CR^b$=$CR^c$—Z, where Z is an electron withdrawing group as defined herein and each of $R^a$, $R^b$ and $R^c$ is independently hydrogen or carbon atom containing group. The α,β-unsaturated compounds of the invention can also have other unsaturated bond(s) that is conjugated to the α,β-unsaturation. Thus, the term 60 ,β-unsaturated compound includes other extended conjugated compounds, such as α,β- and γ,ϴ- unsaturated compounds as well as other more extended conjugated compounds.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis,* 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow and/or preferred, more preferred and most preferred definitions, if any.

5-Membered heterocyclic compounds using [3+2] annulation: Many natural products and pharmaceutically active compounds have 5-membered heterocyclic ring moiety. While methods are available for producing 5-membered heterocyclic ring systems, they often require a circuitous synthetic route, require expensive reagents, require heavy metals that are toxic to mammals, require extensive protection/deprotection steps, do not provide chiral synthesis or provide a low enantiomeric selectivity, or result in only a moderate to low yield of the 3-pyrroline ring system. Accordingly, there is a continuing need for a general method for producing 5-membered heterocyclic compounds. In particular, there is a need for a diastereomerically or an enantiomerically selective and/or enantiomerically specific synthesis of 5-membered heterocyclic compounds.

One aspect of the invention provides a method for producing various 5-membered heterocyclic compounds, including but not limited to 3-pyrroline compounds and 2,5-dihydrofuran compounds. In some particular embodiments of the invention, chiral 3-pyrroline compounds are produced in a single step by treating conjugated systems with a gamma (in the 3-position) leaving group with a strong base such as lithium diisoropyl amine (i.e., LDA) and reacting the resulting intermediate with chiral Ellman type imines. In some embodiments, the method provides enantiomerically and/or diastereomerically enriched 5-membered heterocyclic compounds. The method of present invention is applicable to a variety of compounds including, but not limited to, aldimines substituted with aryl, phenyl, vinyl, alkyl and other groups of small and large sized in the presence of functional groups. The nucleophile is also flexible and has shown to work for esters, sulfones etc.

This method can be generally described as [3+2] annulation. In one particular embodiment of the invention, the reaction involves deprotonating an α,β-unsaturated compound of the formula:

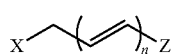

II with a base under condition sufficient to produce a deprotonated intermediate; and reacting said deprotonated intermediate an imine compound of the formula:

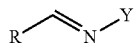

III to produce a 3-pyrroline compound of the formula:

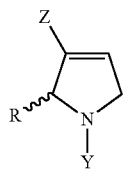

I where n is an integer of 1 to 3, typically n is 1 or 2, and often n is 1; R is hydrogen, alkyl, haloalkyl, aryl, aralkyl, alkenyl, aralkenyl, cycloalkyl, heteroalkyl, heteroaryl or ester functional group; X is a leaving group; Y is an auxiliary group; and Z is an electron withdrawing conjugated group.

It should be appreciated that the compound II can also include one or more substituents on the olefinic bond or the carbon having the "X" leaving group.

In some embodiments, Y is a chiral auxiliary group. One skilled in the art having read the present disclosure can envision and utilize a variety of chiral auxiliary groups. In one particular embodiment, said chiral auxiliary group is a moiety of the formula:

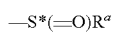

IV where * denotes a chiral center; and $R^a$ is alkyl, cycloalkyl, aralkyl, alkenyl, aralkenyl, heteroalkyl, or heteroaryl.

Typically, the imine compound III has enantiomeric excess of at least 90% ee, typically at least 95% ee, and often at least 99% e.e. Accordingly, in some instances, the 3-pyrroline compound that is produced by the method of the invention is diastereomerically enriched. In particular, the method of invention produces the 3-pyrroline compound I in diastereomeric excess of said 3-pyrroline compound is at least 90% de, typically at least 95% de, and often at least 98% d.e.

In some embodiments, the method of invention includes a step of removing the chiral auxiliary group. Removal of the chiral auxiliary group Y provides a heterocyclic compound in which the 5-membered heterocyclic ring has only one chiral center. Accordingly, the resulting compound is enantiomerically enriched. In some embodiments, removal of the chiral auxiliary group provides a compound whose enantiomerically enrichment is at least about 90%, typically at least about 95%, and often at least 98%.

A wide variety of methods are known to one skilled in the organic chemistry for removing the chiral auxiliary group. Such methods depend on the nature of the chiral auxiliary group that is used in the initial reaction. For example, for a chiral auxiliary group of formula IV, one of the methods for removing the chiral auxiliary group is illustrated in the Examples section.

Exemplary compounds of Formula I that were produced using the method of the invention include, but are not limited to, the following representative compounds:

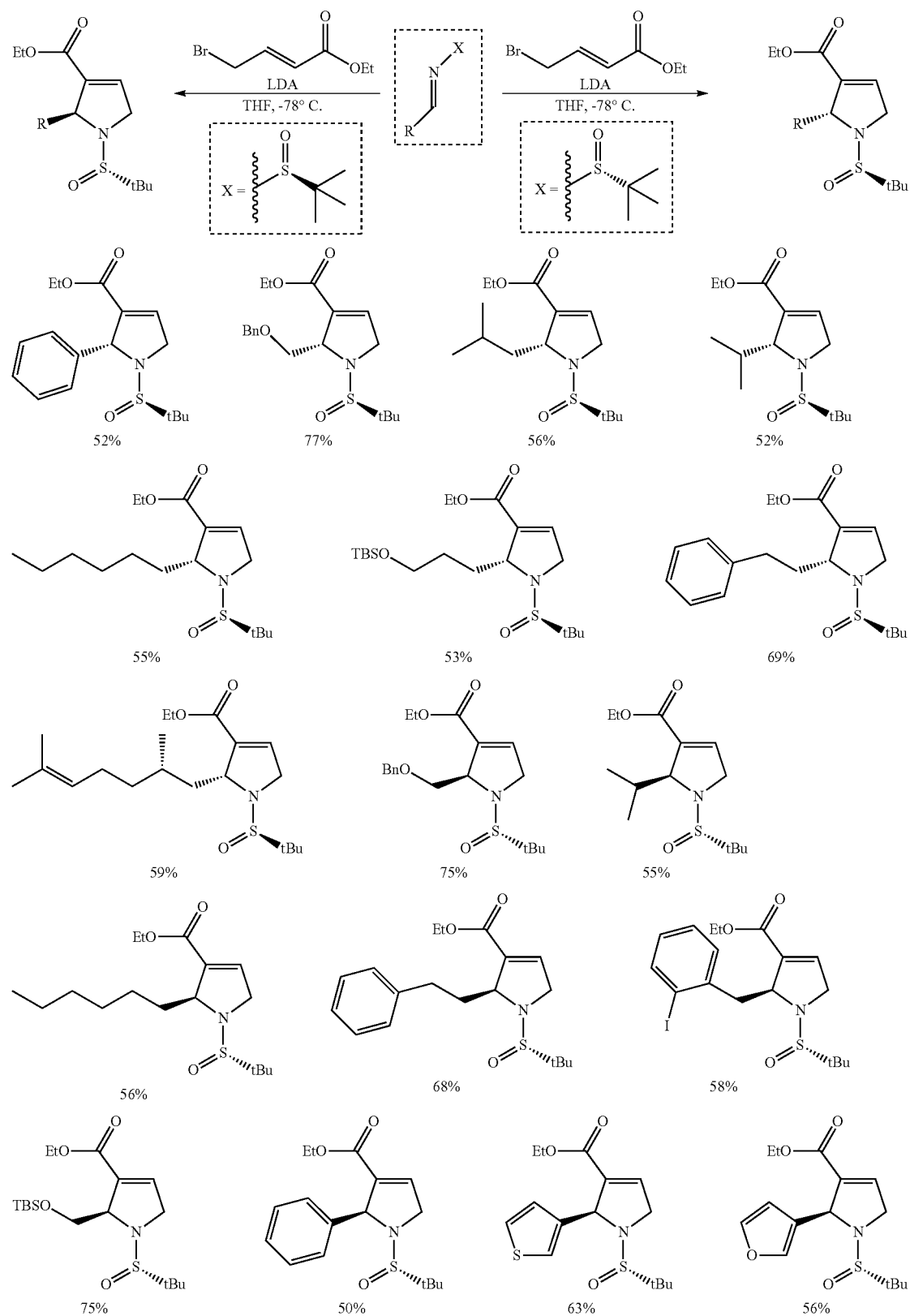

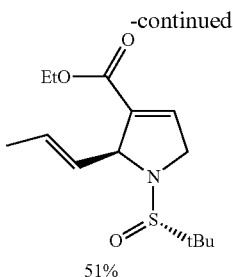

63%

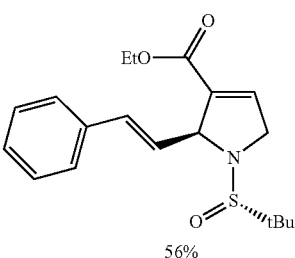

51%

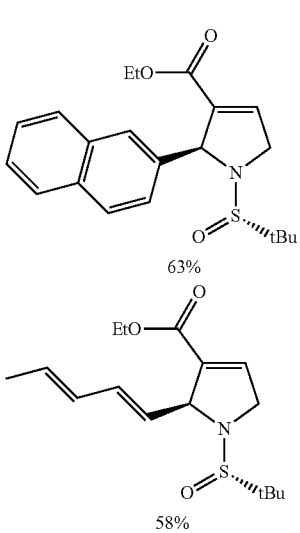

56%

58%

The method of invention is also applicable to other nucleophilic compounds such as aldehydes to produce 2,5-dihydrofuran compounds. In general, the method of invention using an aldehyde is illustrated below:

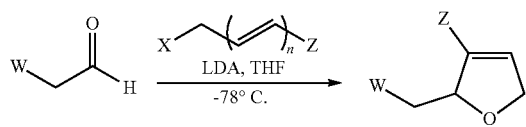

where W is a hydrogen or a substituent such as heteroaryloxy (e.g., benzyloxy), alkyl, alkoxide, etc., and X, n and Z are those defined herein.

The base used in deprotonating Compound II is generally a sterically hindered or relatively non-nucleophilic base, such as LDA, t-BuLi, lithium 2,2,6,6-tetramethylpiperidine, anion of hexamethyldisilazane (e.g., MHMDS, where M is Li, K, or Na) and the like.

Another aspect of the invention provides a process for producing a 3-pyrroline compound of the formula:

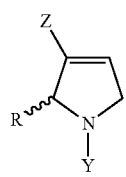

I

The process generally includes contacting an α,β-unsaturated compound of the formula:

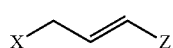

II with a sterically hindered base to produce a reaction mixture; and adding an imine compound of the formula:

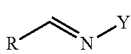

III to said reaction mixture under conditions sufficient to produce said 3-pyrroline compound, where R is hydrogen, alkyl, haloalkyl, aryl, aralkyl, alkenyl, aralkenyl, cycloalkyl, heteroalkyl, heteroaryl or ester functional group X is a leaving group; Y is an auxiliary group; and Z is an electron withdrawing conjugated group.

Synthesis of fluorinated heteroaromatic compounds: Indole structure is present in a wide variety of both natural and synthetic compounds. These core structures are found in many therapeutically useful compounds as well as in various catalytic compounds, dyes, polymers, and other useful chemical compounds. Often conventional syntheses of these useful compounds start with the indole core structured compounds. While some methods are available for producing the indole core structure, they often require a relatively harsh reaction conditions, use of a metal catalyst, or both.

Using a metal catalyst for producing a therapeutically useful compounds (i.e., pharmaceutically active compounds) with an indole core structure limits usefulness of such synthetic methods as any trace amount of metal catalyst must be removed in order to avoid any toxic effects of metal. Even if one can effectively remove the metal, use of a metal catalyst increases the overall cost of producing pharmaceutically active compounds as additional step(s) are needed for removing the metal. Accordingly, there is a need for a procedure or a method for producing compounds comprising indole core structure that does not require a metal catalyst.

Thus, another aspects of the invention provide a process and a method for producing various indole compounds without the need for a metal catalyst. Without being bound by any theory, it is believed that the process of the invention involves an oxidative dearomatization of an aromatic compound which then reacts with a nucleophile. Subsequent rearomatization then affords an indole compound. The process of the invention utilizes mild reaction conditions to achieve a net C—H activation of an aromatic compound. The overall reaction involves replacement of hydrogen atom on the aromatic compound by the nucleophile to produce the intermediate. This intermediate can be isolated and converted to other compounds or it can be rearomatized to produce an indole compound.

The invention also provides various compounds including a compound of Formula IIIA infra, indoles.

One particular aspect of the invention provides a process for producing a fluoroalkyl-substituted heteroaryl compound of the formula:

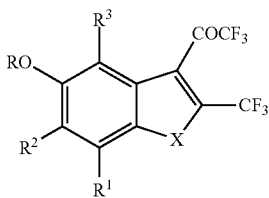

IA comprising contacting an aromatic compound of the formula:

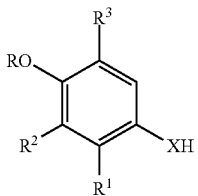

IIA with hexafluoroacetylacetone (Hfacac) under conditions sufficient to produce an intermediate; and contacting said intermediate with an acid under conditions sufficient to produce a fluoroalkyl-substituted compound of Formula IA, where R is alkyl; X is —NR$^a$—, wherein R$^a$ is hydrogen, alkyl or a nitrogen protecting group; and each of R$^1$, R$^2$ and R$^3$ is independently hydrogen, alkyl, haloalkyl, halide, vinyl, alkynyl, CHO, C(=O)R$^b$ (ketone), CO$_2$R$^c$ (ester), OR$^d$, OSO$_2$R$^e$, aryl and heteroaryl, wherein each of R$^b$, R$^c$, R$^d$, and R$^e$ is independently alkyl or aryl.

In some embodiments, said step of producing said intermediate further comprises adding an oxidizing agent. Exemplary suitable oxidizing agents include, but are not limited to, PhI=O, Ar$^a$—I(OCOR$^f$)$_2$, Pb(OCOR$^f$)$_4$, or a mixture thereof, wherein Ar$^a$ is aryl and each of R$^f$ is independently alkyl or aryl. In one particular embodiment, Ar$^a$ is phenyl. In other embodiments, R$^f$ is methyl. In one specific embodiment, phenyliodine diacetate (i.e., Ar$^a$ is phenyl and R$^f$ is methyl) is added during the step of producing the intermediate. The amount of phenyliodine diacetate added to the reaction mixture can vary significantly depending on a wide variety of factors, such as the reaction time, reaction temperature, reaction pressure, etc. Generally, the amount of phenyliodine diacetate added to the reaction mixture ranges from about 1 equivalent to about 10 equivalent, typically 1 equivalent to 6 equivalent and often 1 equivalence to 3 equivalence, relative to the amount of the compound of Formula IIA, is added to the reaction mixture. In one particular embodiment, at least 1 equivalent of phenyliodine diacetate is used to produce the intermediate.

The step of producing the intermediate typically involves using an inert organic solvent. An "inert organic solvent" refers to a solvent that does not directly participate in the reaction, at least not in any significant or noticeable manner. Suitable organic solvents for the step of producing the intermediate include, but are not limited to halogenated alcohols (such as trifluoroethanol), diethyl ether, tetrahydrofuran, dichloromethane, chloroform, dimethylformamide (DMF), acetonitrile, and the like, or a mixture thereof. Typically, the oxidizing agent and the Hfacac is added to the solvent prior to adding a compound of Formula II to the reaction mixture. Typical reaction temperature for producing the intermediate ranges from 0° C. to about 50° C., often from 10° C. to about 30° C., and more often from about 15° C. to about 25° C. It should be appreciated however, the scope of the invention is not limited to these temperature ranges as the reaction temperature can vary significantly depending on a wide variety of factors such as, but not limited to, reactivity of the compound of Formula II, reaction time, oxidizing agent used, concentration of each reagents used, the nature of the solvent used, etc.

The reaction time for producing the intermediate can also vary significantly depending on the number of factors, such as those enumerated above. However, at room temperature, the reaction time typically ranges from about 0.1 hr to about 10 hr, often from about 0.5 hr to about 5 hr, and more often from about 0.5 hr to about 2 hr.

The amount of Hfacac added to the reaction mixture can vary significantly depending on a wide variety of factors, such as those described above. Generally, the amount of Hfacac added to the reaction mixture ranges from about 1 equivalent to about 10 equivalent, typically 1 equivalent to 6 equivalent and often 1 equivalence to 3 equivalence, relative to the amount of the compound of Formula IIA, is added to the reaction mixture. In one particular embodiment, at least 1 equivalent of Hfacac is used to produce the intermediate.

Without being bound by any theory, it is believed that the intermediate that is produced in a reaction between compound of Formula IIA and Hfacac and typically in the presence of an oxidizing agent is of the formula:

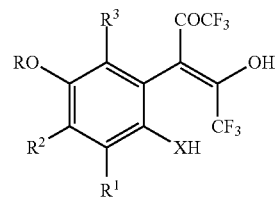

IIIA where R, R$^1$, R$^2$, R$^3$ are those defined herein. It should be appreciated that Compound of Formula IIIA can exist in (or be in equilibrium with) its tautomer and/or its geometric isomer. For example, the vinyl hydroxyl group can be in its carbonyl form (i.e., tautomer), and/or the E-vinyl group can be in Z-geometric isomer form. Thus, for the sake of clarity and brevity, while Compound of Formula IIIA is drawn with the tautomeric and geometric form shown above, unless explicitly stated any reference and/or claim to Compound of Formula III include its tautomeric and geometric isomers.

The process of the invention includes contacting the intermediate with an acid under conditions sufficient to produce a fluoroalkyl-substituted compound of Formula IA. Suitable acids include organic acids (e.g., carboxylic acids including mono- and di-carboxylic acids), hydrochloric acid, sulfuric acid, phosphoric acid and Lewis acids.

Another aspect of the invention provides a process for producing a fluoroalkyl-substituted heteroaryl compound of the formula:

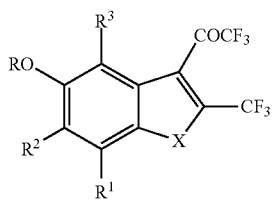

IA comprising (i) adding hexafluoroacetylacetone (Hfacac) to a solution of phenyliodine diacetate to produce a reactive intermediate solution; (ii) adding an aromatic compound of the formula:

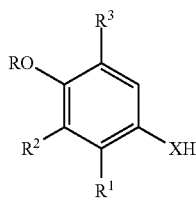

IIA to said reactive intermediate solution under conditions sufficient to produce an intermediate; and (iii) contacting said intermediate with an acid under conditions sufficient to produce a fluoroalkyl-substituted compound of Formula IA, where R is alkyl; X is $-NR^a-$, wherein $R^a$ is hydrogen, alkyl or a nitrogen protecting group; and each of $R^1$, $R^2$ and $R^3$ is independently hydrogen, alkyl, haloalkyl, halide, vinyl, alkynyl, CHO, C(=O)$R^b$ (ketone), CO$_2$$R^c$ (ester), O$R^d$, OSO$_2$$R^e$, aryl and heteroaryl, wherein each of $R^b$, $R^c$, $R^d$, and $R^e$ is independently alkyl or aryl.

Still other aspects of the invention provide indole compounds. Exemplary Compounds of Formula IA include, but are not limited to, those where X is —NH— provided Compound of Formula IA does not include the following indole compounds:

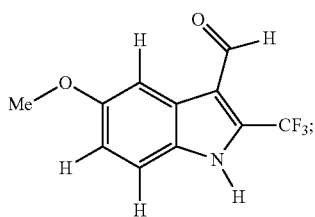

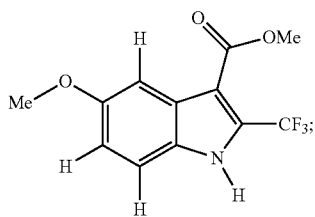

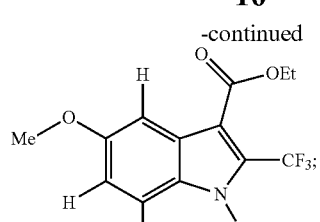

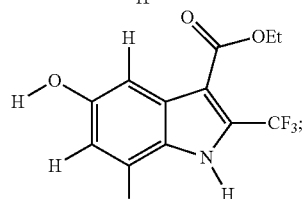

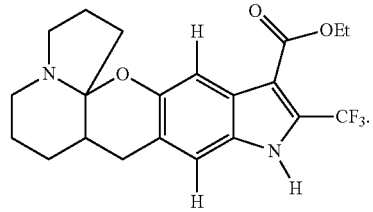

It should be appreciated that combinations of the various groups described herein form other embodiments. For example, in one particularly embodiment, the oxidizing agent is $Ar^a$ is phenyl and $R^f$ is methyl. In this manner, a variety of compounds, including those of Compounds of Formulas IA, IIA and IIIA, are embodied within the present invention.

Meta-alkylation of phenols: Conventional alkylation methods of a phenolic compound, such as Friedel-Craft alkylation reaction, typically provide an ortho- and/or para-substituted alkyl phenols. While other phenolic substitution reactions have been developed, they typically require expensive reagents and/or relatively harsh reaction conditions, e.g., elevated temperature and/or relatively long reaction time. Other methods for alkylation reaction in a meta-position utilize indirect alkylation followed by further transformation to produce an alkyl substituents. For example, acylation using Friedel-Craft produces meta-substituted acyl phenolic compounds. The acyl group is then reduced to produce meta-alkyl substituted phenols. Such indirect methods increase time and cost. More significantly, substitution of an alkyl group in a meta-position of a phenolic compound to date has not been achieved under a mild reaction condition or in a relatively high yield.

Another aspect of the invention provides a relatively mild method of producing a direct meta-alkyl substituted phenol compounds. In one particular embodiment, the method involves alkylating a phenolic compound with an alkylating agent. Such a method produces a meta-alkyl substituted phenolic compound. The method of invention includes contacting a phenolic compound with an oxidizing agent under conditions sufficient to produce a reactive intermediate compound. The reactive intermediate is than contacted with an alkylating agent under conditions sufficient to produce a meta-alkyl substituted phenolic compound. It should be appreciated that the intermediate need not be isolated. Thus, in some embodiments, the entire reaction can be carried out in a single reaction vessel. The meta-alkyl substituted phenolic compound can be further reacted with an electrophilic moiety prior to isolation or work-up.

Some aspects of the invention provide a method for directly alkylating a phenolic compound with an alkylating agent. As used herein, the term "directly alkylating" refers to production or synthesis of a phenolic compound in which the alkyl substituent is produced without any further functional group manipulation of the alkyl-substituent. It should be noted that there maybe a typical "work-up" process that may be required to isolate the alkyl-substituted phenolic compounds. bThe term "meta-alkyl substituted phenolic compound" refers to a phenolic compound in which the alkyl-group is in a meta-position relative to the hydroxyl group of the phenol compound. The term "work-up" refers to stopping the reaction, for example, by adding a reaction quenching reagent to inhibit further reaction. For example, by adding water, silica gel, etc. to prevent further substitution reaction. Unless stated or context require otherwise, any substituent's position refers to position with respect to the hydroxyl group of the phenol compound. Thus, the term "meta-position" refers to position 3- or 5-relative to the hydroxyl group (i.e., 1-position) of the phenol compound. Similarly, the term "ortho-" refers to position 2- or 6-relative to the hydroxyl group.

The method of invention includes contacting a phenolic compound with an oxidizing agent under conditions sufficient to produce a reactive intermediate compound. Without being bound by any theory, it is believed that the reactive intermediate compound is one in which the benzene ring system has lost its aromaticity. Generally, the reactive intermediate is not isolated. However, the oxidizing agent can be removed either by quenching with another reagent and/or by separation. But it should be appreciated that the scope of the invention includes using the reactive intermediate directly. Typically, the reaction between the phenolic compound and an oxidizing agent is carried out at a reaction temperature of about 50° C. or less, often at about 25° C. or less, more often at about 10° C. or less, and most often at about 0° C. or less. The term "about" refers to±20%, typically±10%, and often±5% of the numeric value. However, it should be appreciated that the scope of the invention is not limited to these particular reaction temperatures. The reaction temperature can vary depending on a variety of factors including, but not limited to, the phenolic compound, reaction time, reaction solvent, etc.

The reaction time generally ranges from a few (e.g., 2, 5, or 10) minutes to a few (e.g., 2, 3, or 5) hours. Often the reaction time ranges from about 10 minutes to about 3 hours, more often the reaction time ranges from about 20 minutes to about an hour, and most often the reaction time ranges from about 30 minutes to about 60 minutes. However, it should be appreciated that the scope of the invention is not limited to these particular reaction times. The reaction time can vary depending on a variety of factors including, but not limited to, the phenolic compound, reaction temperature, solvent, etc.

In some embodiments, the oxidizing agent comprises a compound of the formula $ArI(OC(=O)R)_2$, $Pb(OC(=O)R)_4$, or a combination thereof, where each of R is independently an alkyl, haloalkyl, cycloalkyl, optionally substituted aryl, aralkyl or (cycloalkyl)alkyl, and Ar is an aryl group, which can be optionally substituted with carbon atoms or other heteroatoms, including but not limited to halogens (F, Cl), nitrogen, oxygen, or sulfur containing functionalities. The term "optionally substituted" means that one or more substituent may be present within the aromatic ring structure. When two or more substituents are present in an aryl group, each substituent is independently selected. Typical substituents include, but not limited to, halo, alkyl, haloalkyl, alkoxy, $-COX_nR$ (where n is 0 or 1, X is $-O-$ or $-NR^a-$, where $R^a$ is hydrogen, alkyl, or a nitrogen protecting group, and R is alkyl or optionally substituted phenyl), etc.

The reaction between a phenolic compound and an oxidizing agent can be carried out in a wide variety of organic solvents. Suitable reaction solvents include, but are not limited to, toluene, benzene, xylene, trifluorotoluene, chloroform, dichloromethane, hexane, pentane, or a mixture thereof. The solvent can also include water.

The amount of oxidizing agent used typically ranges from about 0.9 equivalent to about 5 equivalents, often from about 1 equivalent to about 3 equivalents, and most often from about 1 equivalent to about 2 equivalents. However, it should be appreciated that the scope of the invention is not limited to these amounts of oxidizing agent used.

Regardless of the nature of the reactive intermediate produced, methods of the invention include contacting the reactive intermediate with an alkylating agent. Generally, the reactive intermediate is contacted with an alkylating agent under conditions sufficient to produce a meta-alkyl substituted phenolic compound. It should be appreciated that the intermediate need not be isolated. Thus, in some embodiments, the entire reaction can be carried our in a single reaction vessel. In some embodiments, the alkylating agent is a compound of the formula $R^1B((O)_nR^2)((X)_nR^3)$, where $R^1$ is an alkyl that is typically "transferred", i.e., alkylated, to the phenolic compound, each n is independently 0 or 1, each of $R^2$ and $R^3$ is independently alkyl, or $R^2$ and $R^3$ together with the atom to which they are attached to form a cyclic moiety. Depending on the reaction conditions and the $R^1$, $R^2$ and $R^3$ groups, as well as the presence of oxygen atom(s), secondary and tertiary alkyl groups may be preferentially transferred over primary and cyclic alkyl groups. Primary alkyl group can be selectively transferred by a variety of means. One method of transferring a primary group is to use a boron reagent with identical primary alkyl groups (e.g., $R^1$, $R^2$ and $R^3$ are same and n is 0). Alternatively, one can use a borate reagent, e.g., where n is 1, i.e., a compound of the formula: $R^1B(OR^2)(OR^3)$. One example of a borate reagent that can be used to alkylate a primary alkyl group is of the formula:

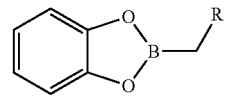

A where "$-CH_2R$" is the alkyl moiety that is alkylate into a phenolic compound. Compound A can be readily prepared, e.g., by hydroborating an alkene compound of the formula $CH_2=CH_2R$ with catechol borane.

The reaction temperature for alkylation of the reactive intermediate with an alkylating reagent is typically about 80° C. or less, often about 50° C. or less, and more often about 30° C. or less. However, it should be appreciated that the scope of the invention is not limited to these reaction temperatures as a variety of factors can influence the reaction temperature. Generally, a suitable reaction temperature is determined by the substituents that are present on the phenolic compound (i.e., the "nature of the phenolic compound"), reaction time, reactivity of the alkylating agent, reaction solvent used, and a variety of other factors that influence the reaction including concentration of each reactants.

The reaction time for alkylation of the reactive intermediate can vary significantly depending on a variety factors discussed herein. Generally, however, the reaction time for alkylation of the reactive intermediate is about a few hours (e.g., 10) hours or less, typically about 5 hours or less, often about 3 hours or less, more often about 2 hours or less, and most often about 1 hour or less.

The solvent for alkylation of the reactive intermediate may include the solvent that is used in generating the reactive intermediate. Other suitable solvents include, but are not limited to, any organic solvent that is relatively non-reactive to the alkylating agent. It should be appreciated that one skilled in the art of organic chemistry can readily recognize suitable organic solvents. Exemplary solvents that can be used in alkylating the reactive intermediate include, but are not limited to, organic solvents used in generating the reactive intermediate, ethers (such as diethyl ether and tetrahydrofuran, i.e., THF), alkane solvents (e.g., hexane, pentane, etc.), chloroform, dichloromethane, toluene, benzene, xylene, dimethylformamide (DMF), and the like.

and F), double and triple bond substituents, provided at least one of $R^2$, $R^3$, $R^4$ and $R^5$ is hydrogen. Often at least one of $R^2$ and $R^4$ is hydrogen.

As illustrated in Scheme A above, the reactive intermediate compound can be accessed in at least two ways, depending if an external nucleophile, most commonly an alcohol is used along with the oxidant. This also means that the meta-alkylated phenolic product can have a different ortho-substituent (relative to the phenol hydroxyl group) than the starting phenol. Therefore, the ortho-substituent can be interchangeable.

The meta-alkyl substituted phenolic compound can be further reacted with an electrophilic moiety prior to isolation or work-up. This allows one to add a second substituent in situ, i.e., without the need to isolate the alkylated phenolic compound. The electrophilic moiety can be a separate compound or it can be present as a substituent on the phenolic compound itself, in which case the resulting substitution leads to a ring formation. Some of the suitable electrophilic reaction of the alkylated phenolic compound is illustrated schematically in FIGS. 1 and 2.

Scheme A

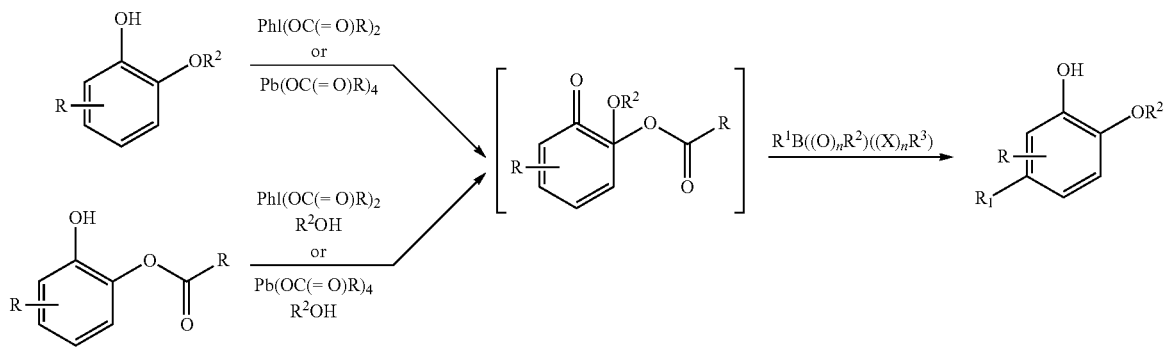

The phenolic compound (i.e., the starting material) can be any phenolic compound having other substituents on the phenyl ring system. Generally, however, the phenolic compound includes an ortho- (relative to the phenol hydroxyl group) substituent. Often the ortho-substituent is an alkoxy, aryloxy, acetoxy and the like, a fused ring ether or a lactone, e.g., a moiety of the formula —$OR^1$, where $R^1$ is alkyl, aryl, acetyl, fused ring ether, or a lactone, respectively. In one particular embodiment, the phenol compound is of the formula:

B

Figure 2:
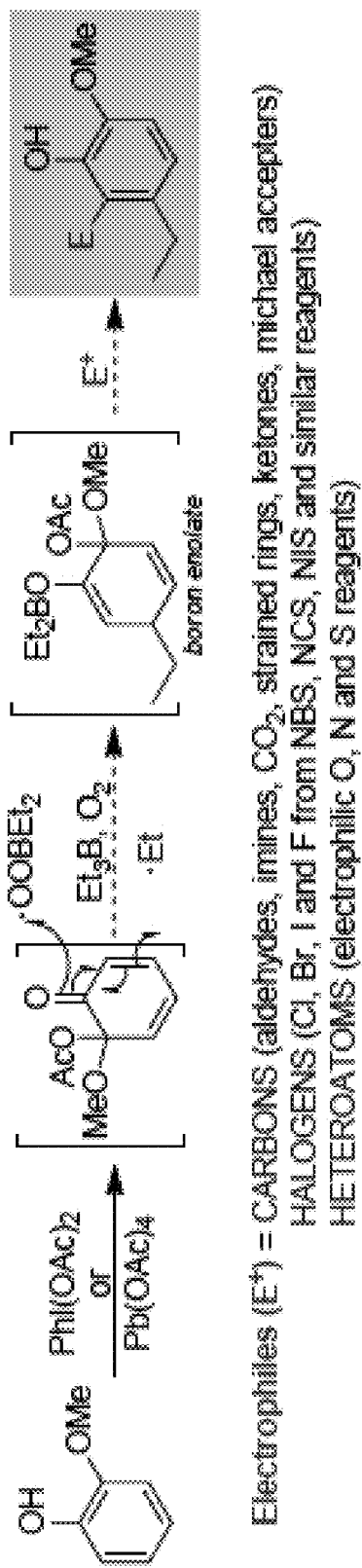
FIG. 2 is another schematic illustration of reaction scheme for electrophilic reaction of alkylated phenolic compounds.

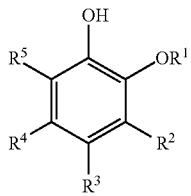

where $R^1$ is alkyl, aryl or a fused ring ether. As used herein, the term "fused ring ether" includes Compound of Formula B wherein $R^1$ together with $R^2$ forms a cyclic ether. In such instances, $R^2$ may include an oxygen atom that is attached to the aromatic ring system. Typically, each of $R^2$, $R^3$, $R^4$ and $R^5$ is independently hydrogen, alkyl, aryl, aldehydes, ketones, esters, nitriles, nitro, azides, halide (e.g., I, Br, Cl It should be appreciated that the scope of the reaction is not limited to those illustrated in FIGS. 1 and 2 as any suitable electrophilic moiety can be used in a second reaction with the alkylated phenolic compound. It should also be appreciated that the reaction mechanisms shown in FIGS. 1 and 2 are provided solely for the illustration purposes and do not limit the scope of the invention. In fact, it is possible that the electrophilic substitution involves some other reaction mechanisms.

As discussed herein, in some embodiments, the method of the invention further comprises the steps of contacting the meta-alkyl substituted phenolic compound with an electrophilic moiety to produce a phenolic compound comprising an alkyl substituent and an electrophilic substituent.

In some instances, the phenolic compound further comprises an ortho-substituted electron donating group, e.g., —$OR^1$ in Compound of Formula B. However, it should be appreciated that the scope of the invention is not limited to electron donation group of the formula —$OR^1$. In general, any electron donating group can be present in the ortho-position of the phenolic compound. Suitable electron donating groups include, but are not limited to, alkyl and aryl groups as well as other heteroatom (e.g., N or S) substituents.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

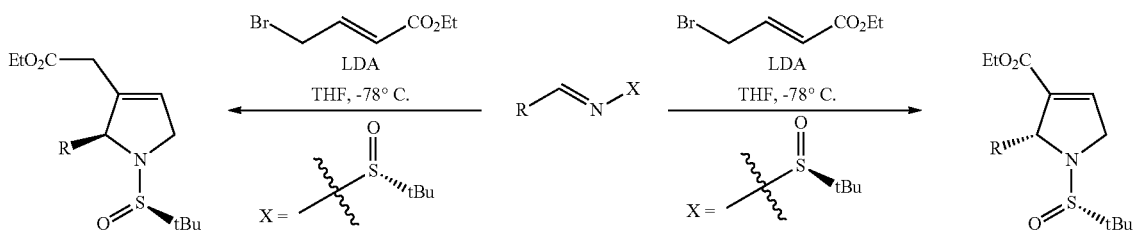

Example 1

General Procedure for the Synthesis of 3-Pyrrolines:

To a round bottomed flask equipped with magnetic stir bar and diisopropyl amine (3.0 eq in THF, −78° C.) was added n-butyl lithium (3.0 eq) then warmed to 0° C. and allowed to stir for 15 minutes. The lithium isopropyl amide (LDA) solution was then cooled to −78° C. and additional THF was added such that the overall concentration is 0.1 M based on the imine. Neat ethyl 4-bromocrotonate (75%, 1.2 eq.) was added to the LDA solution at −78° C. and stirred for 30 minutes. A solution of the respective imine (1.0 eq. in THF) was then added using a syringe pump at a rate of 0.5 mL/h and the reaction kept at −78° C. and allowed to stir for additional 4-8hours. The reaction was then quenched with saturated ammonium chloride and allowed to warm to room temperature, extracted using ethyl acetate (3 times), washed with brine. The combined organic extracts were dried using anhydrous sodium sulfate then solvent evaporated. Crude material was purified by flash column chromatography (silica gel, 20-40% EtOAc in hexanes) to afford the 3-pyrroline compound.

Some of the representative 3-pyrroline compounds produced by using the General Procedure described herein are shown below:

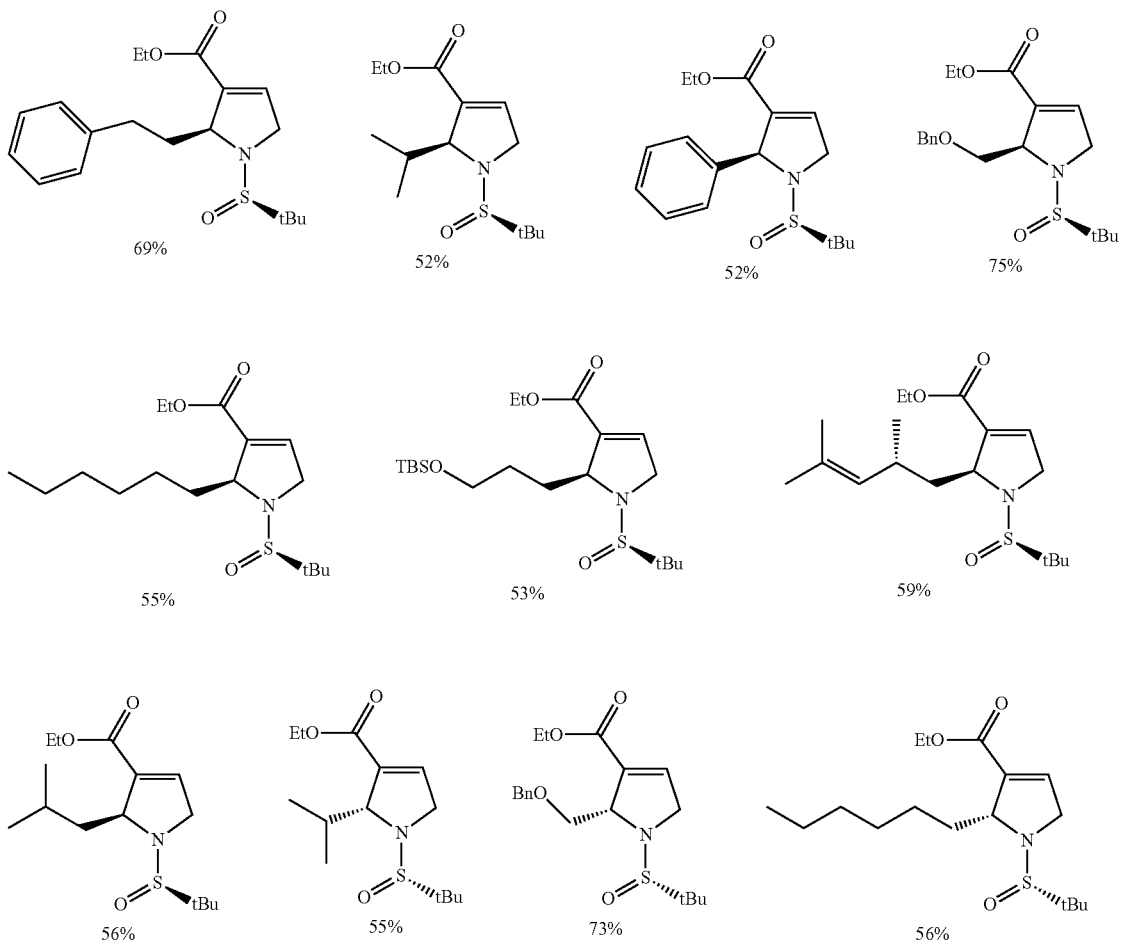

-continued
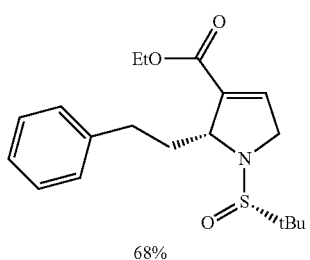
68%
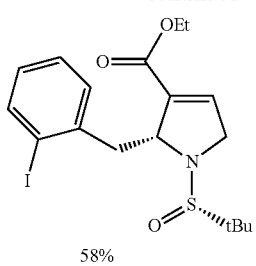
58%
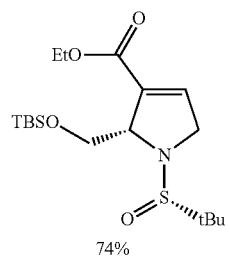
74%
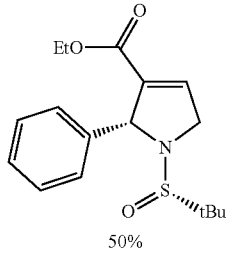
50%
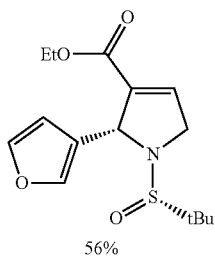
56%
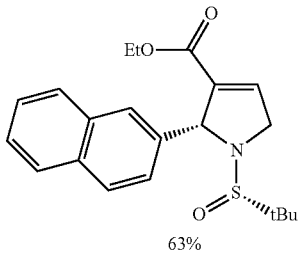
63%
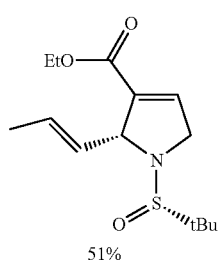
51%
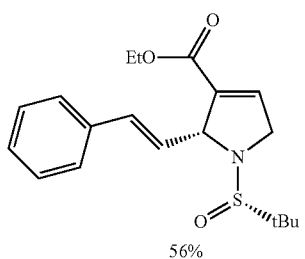
56%
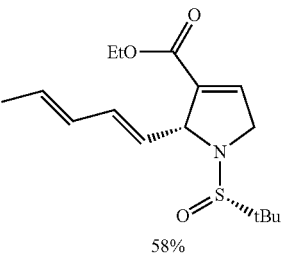
58%
Example 2
Asymmetric Synthesis of (+)-Elacomine:
Using the procedure described in Example 1 above, enantiomerically enriched (+)-elacomine is produced using the synthetic scheme shown below:
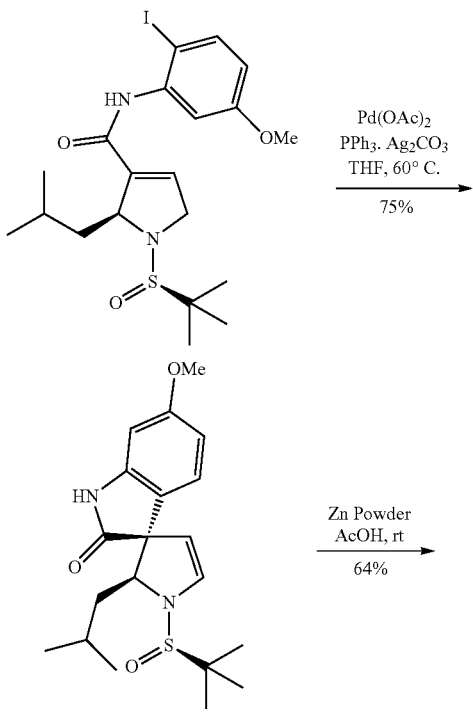

25

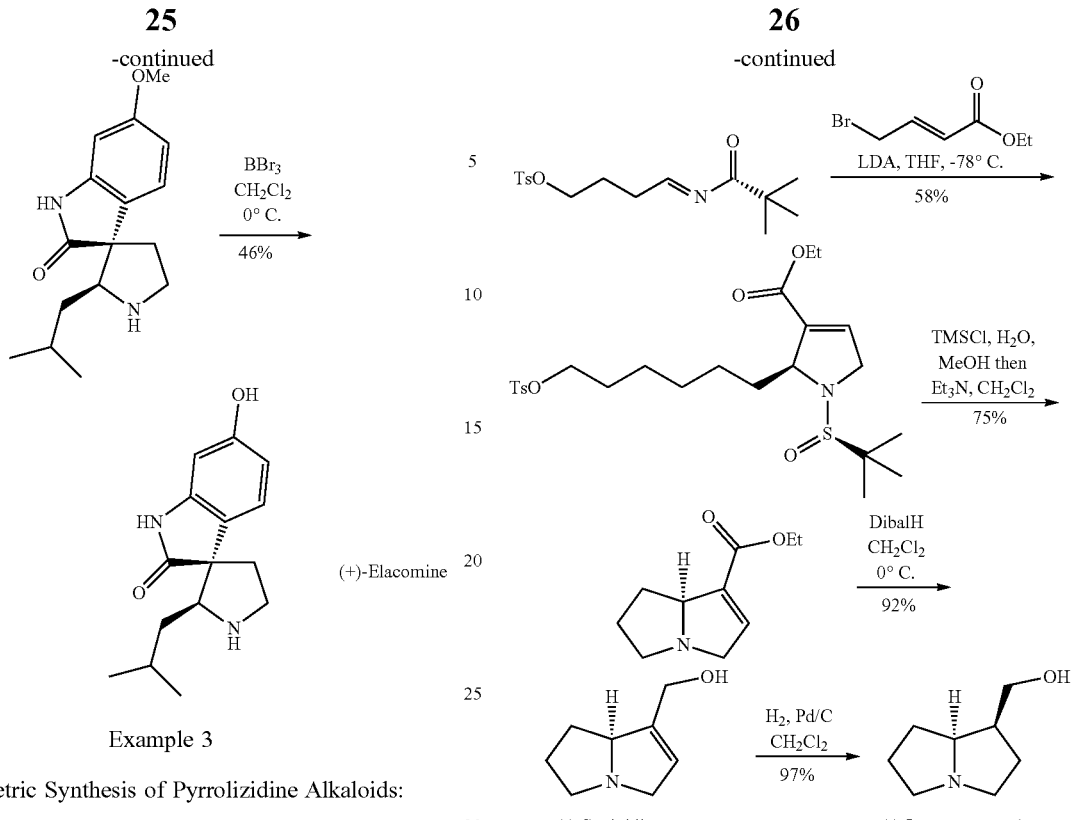

Example 3

Asymmetric Synthesis of Pyrrolizidine Alkaloids:

Using the procedure described in Example 1 above, enantiomerically enriched (+)-supinidine and (−)-isoretronecanol are produced using the synthetic scheme shown below:

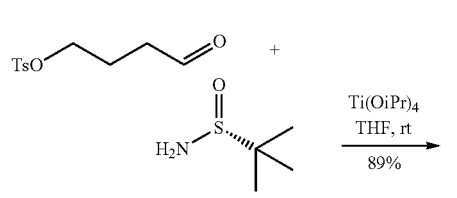

26

Example 4

Asymmetric Synthesis of Other Nitrogen Ring Containing Compounds:

Using the procedure described in Example 1 above, diastereomerically enriched nitrogen ring containing compounds are produced using the synthetic scheme shown below:

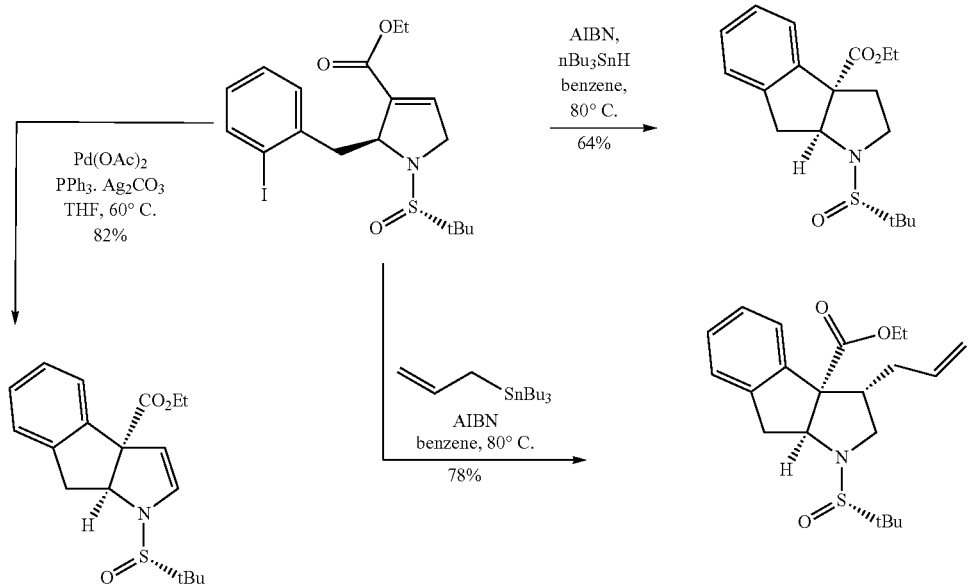

Example 5

Annulation of Aldehydes:

Using the procedure similar to that described in Example 1 above, annulation of aldehydes provided 2,5-dihydrofuran compounds as shown below:

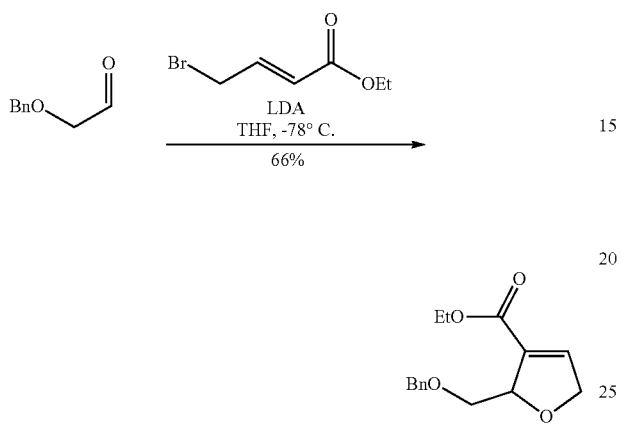

Example 6

Annulation of other α,β-Unsaturated Compounds:

Using the procedure described in Example 1 above, diastereomerically enriched nitrogen ring compounds were obtained from other ≠,β-unsaturated compounds as shown below:

Example 7

Annulation of α,β,γ,∂-diunsaturated Compound:

Using the procedure described in Example 1 above, diastereomerically enriched nitrogen ring compounds were obtained from α,β,γ,∂-diunsaturated compound as shown below:

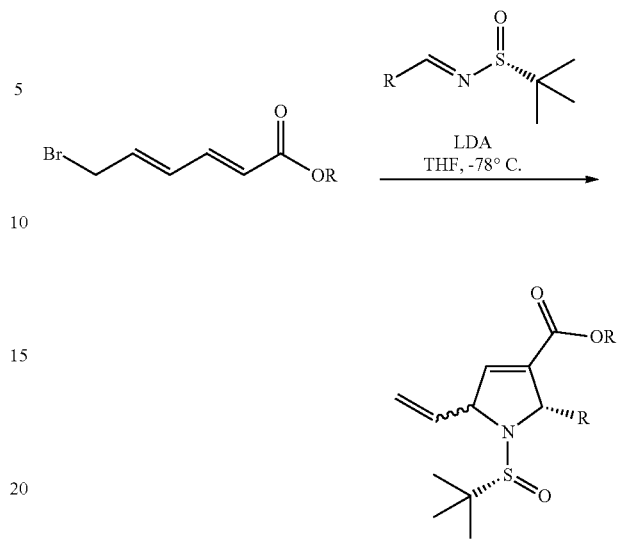

Example 8

Reaction Conditions:

Using the procedure described in Example 1 above, various reaction conditions were used as illustrated below to determine the affect on the yield of the product:

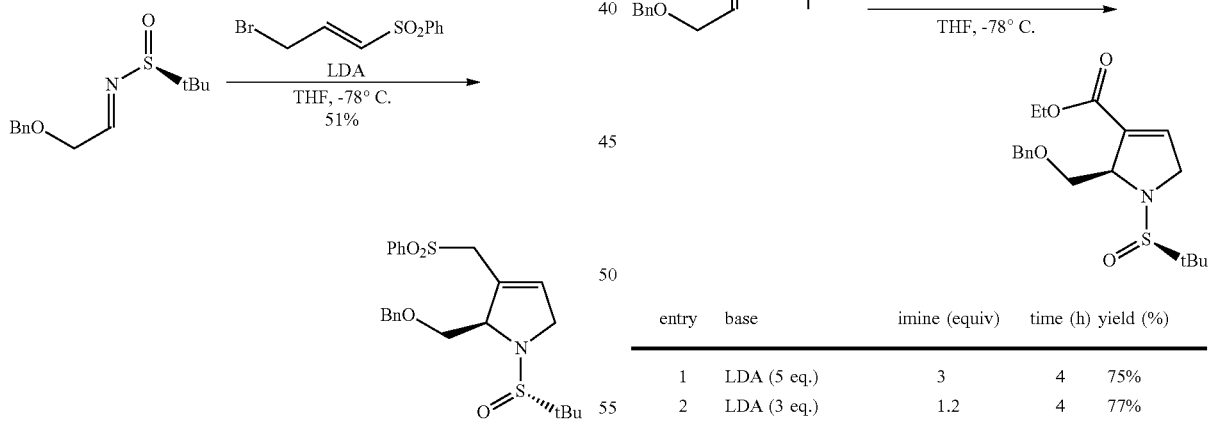

| entry | base | imine (equiv) | time (h) | yield (%) |
|---|---|---|---|---|
| 1 | LDA (5 eq.) | 3 | 4 | 75% |
| 2 | LDA (3 eq.) | 1.2 | 4 | 77% |
| 3 | LDA (3 eq.) | 1.2 | 4 | 60%[a] |
| 4 | LDA (3 eq.) | 1.2 | 4 | 52%[b] |
| 5 | LDA (3 eq.) | 1.2 | 4 | 58%[c] |
| 6 | LDA (3 eq.) | 1.2 | 4 | 55%[d] |
| 7 | LDA (3 eq., Et$_2$O) | 1.2 | 4 | 49% |
| 8 | LDA (3 eq., 0° C.) | 1.2 | 4 | 0% |
| 9 | LDA (2 eq.) | 1.2 | 6 | 63% |
| 10 | LDA (1 eq.) | 1.2 | 6 | 22% |
| 11 | NaHMDS (3 eq.) | 2 | 6 | 43% |
| 12 | NaHMDS (2 eq.) | 1.2 | 6 | 38% |

| 13 | LiHMDS (2 eq.) | 1.2 | 6 | 31% |
| 14 | KOtBu (2 eq.) | 1.2 | 6 | <10% |

Standard reaction conditions: Crotonate added to base in THF at −78° C. followed by slow addition of imine (0.5 mL/hour).
[a]1.0 mL/hour addition of imine,
[b]2.0 mL/hour addition of imine,
[c]imine and crotonate added simultaneously to a cooled LDA solution,
[d]LDA added to a solution of imine and crotonate at −78° C.

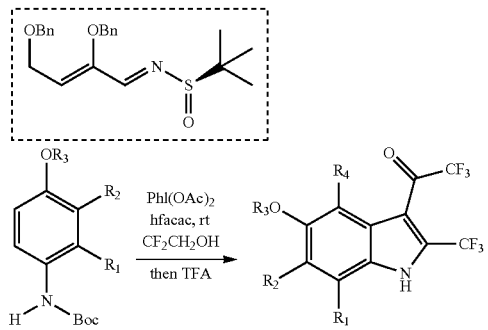

Example 9

General Procedure for Synthesis of Indoles:

This example illustrates a typical synthesis of indole compounds using the method of the invention.

To a 4 mL vial, phenyliodine diacetate (PIDA, 258 mg, 0.8 mmol, 2.0 eq) and trifluoroethanol (TFE, 1.2 mL) were added and the contents were stirred at room temperature. Hexafluoroacetylacetone (Hfacac, 170 µL, 1.2 mmol, 3.0 eq) was syringed in, followed by the addition of aniline derivative (0.4 mmol, 1.0 eq) in trifluoroethanol (0.4 mL). The reaction mixture was stirred and trifluoroacetic acid (TFA, 0.3 mL, 4.0 mmol, 10.0 eq) was syringed in and stirred overnight. The reaction mixture was concentrated in-vacuo, and the residue was dissolved in ethyl acetate (EtOAc, 15 mL) and the organic fraction was washed with saturated NaHCO$_3$ (15 mL). The product was extracted further with ethyl acetate (2×15 mL), and the organic fractions were combined, washed with brine (20 mL), collected, dried with anhydrous Na$_2$SO$_4$, filtered, concentrated in-vacuo, and the residue was purified through dry-loading flash chromatography to give the pure indole derivative.

Using the general procedure above, the following compounds were prepared:

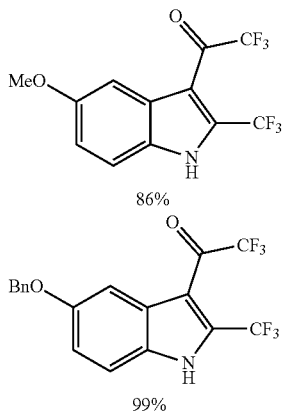

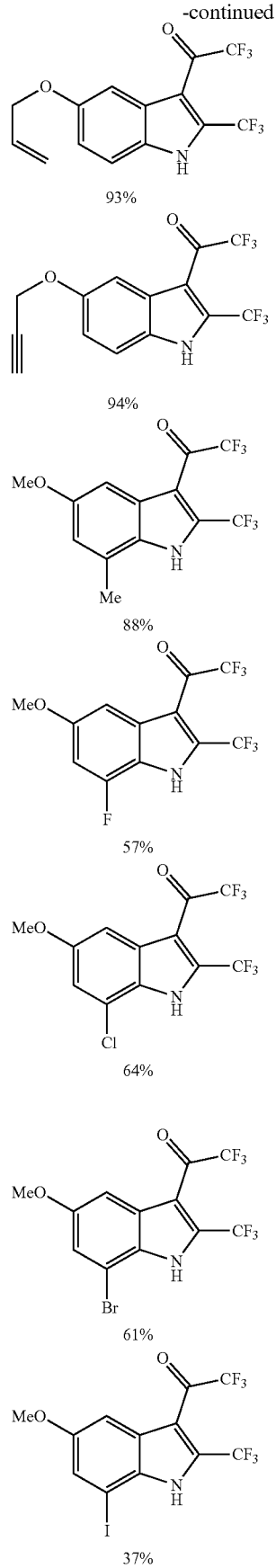

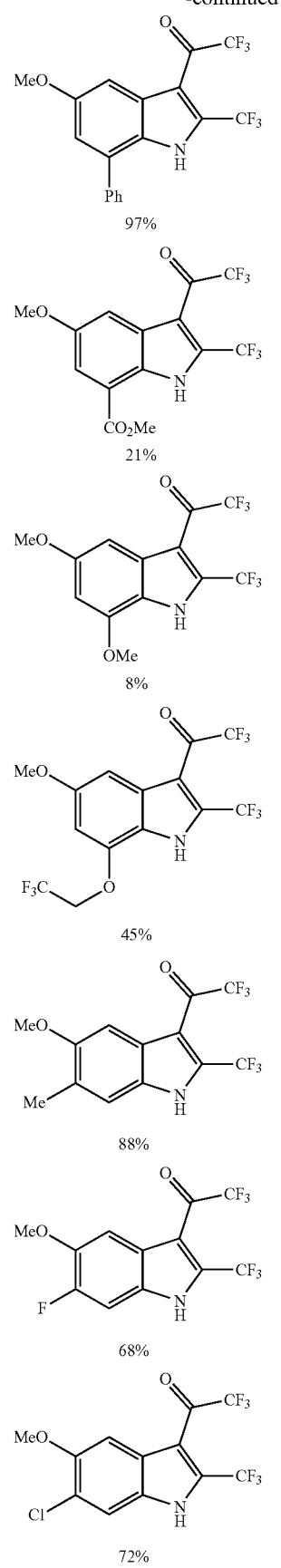
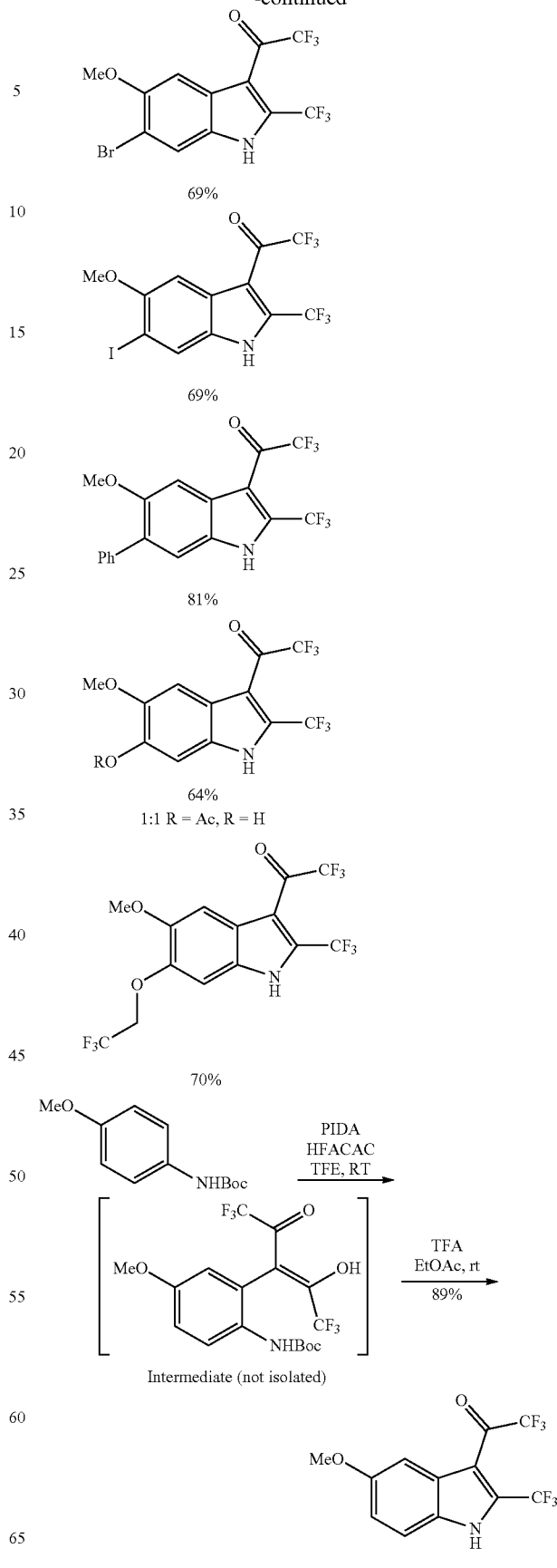

Example 10

Electrophilic Substitution Reaction:

To lead(IV) acetate, trifluorotoluene was added and the solution was stirred at 0° C. Starting material in trifluorotoluene was syringed in, and the reaction was stirred at 0° C. until TLC showed complete consumption of the starting material (avg. 30 min). The ice-bath was removed, the reaction flask was opened, and pinacol was added. After 30 min, the reaction mixture was filtered through an alumina plug and washed thoroughly with trifluorotoluene. To the filtrate, triethylborane was added, followed by air, and the reaction was stirred for 60 min. The reaction mixture was opened, and silica gel was added and the slurry was stirred for 60 min. The slurry was then vacuum filtered through a silica gel pad, and washed thoroughly with ethyl acetate. The filtrate was concentrated /;z to give the crude meta-ethylated phenol, which was purified via flash column chromatography.

Using the general procedure above, the following compounds were prepared from their respective starting materials.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for producing a diastereomerically enriched 3-pyrroline compound of the formula:

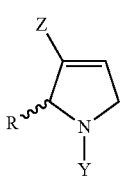

I said method comprising:
deprotonating an α,β-unsaturated compound of the formula:

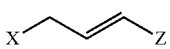

II with a base under condition sufficient to produce a deprotonated intermediate; and
reacting said deprotonated intermediate with an enantiomerically enriched imine compound of the formula:

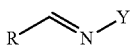

under conditions sufficient to produce said diastereomerically enriched 3-pyrroline compound of Formula I,
wherein
R is hydrogen, alkyl, haloalkyl, aryl, aralkyl, alkenyl, aralkenyl, cycloalkyl, heteroalkyl, heteroaryl or ester functional group;
X is a leaving group;
Y is a chiral auxiliary group of the formula —S*(=O)$R^a$, wherein * denotes a chiral center and $R^a$ is alkyl, cycloalkyl, aralkyl, alkenyl, aralkenyl, heteroalkyl, or heteroaryl; and
Z is an electron withdrawing conjugated group.

2. The method of claim 1, wherein said imine compound of Formula III has enantiomeric excess (e.e.) of at least 90% e.e.

3. The method of claim 2, wherein the diastereomeric excess (d.e.) of said 3-pyrroline compound is at least 90% d.e.

4. The method of claim 3, wherein the diastereomeric excess (d.e.) of said 3-pyrroline compound is at least 95% d.e.

5. The method of claim 1, wherein $R^a$ is alkyl.
6. The method of claim 5, wherein $R^a$ is tert-butyl.
7. The method of claim 1, wherein * is an (S)-isomer.
8. The method of claim 1, wherein * is an (R)-isomer.
9. The method of claim 2, wherein said imine compound of Formula III has enantiomeric excess of at least 95% e.e.
10. The method of claim 2, wherein said imine compound of Formula III has enantiomeric excess of at least 99% e.e.
11. The method of claim 3, wherein the diastereomeric excess of said 3-pyrroline compound is at least 99% d.e.
12. The method of claim 1 further comprising the steps of removing the chiral auxiliary group from said 3-pyrroline compound of Formula I to produce a free 3-pyrroline compound of Formula IA:

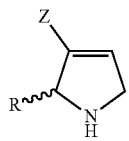

wherein
R and Z are those defined in claim 1.

* * * * *

UNITED STATES PATENT AND TRADEMARK OFFICE
CERTIFICATE OF CORRECTION

PATENT NO. : 10,358,438 B2
APPLICATION NO. : 15/329615
DATED : July 23, 2019
INVENTOR(S) : Jon T. Njardarson et al.

Page 1 of 1

It is certified that error appears in the above-identified patent and that said Letters Patent is hereby corrected as shown below:

In the Specification

Accordingly, please insert a "Statement Regarding Federally Funded Research" section after Line 13 on Column 1 (after the "Cross-Reference to Related Applications" section and before the "Field of the Invention" section" as follows:
--STATEMENT REGARDING FEDERALLY FUNDED RESEARCH
This invention was made with government support under Grant No. CHE1266365 awarded by NSF. The government has certain rights in the invention.--

Signed and Sealed this
Nineteenth Day of November, 2019

Andrei Iancu
*Director of the United States Patent and Trademark Office*